(12) United States Patent
Temple et al.

(10) Patent No.: US 7,901,936 B2
(45) Date of Patent: Mar. 8, 2011

(54) METHOD FOR STIMULATING SELF-RENEWAL OF NEURAL STEM CELLS AND ENHANCING NEUROGENESIS

(75) Inventors: Sally Temple, Slingerlands, NY (US); Qin Shen, Delmar, NY (US); Susan K. Goderie, Ballston Spa, NY (US)

(73) Assignee: Albany Medical College, Albany, NY (US)

( * ) Notice: Subject to any disclaimer, the term of this patent is extended or adjusted under 35 U.S.C. 154(b) by 0 days.

(21) Appl. No.: 11/095,019

(22) Filed: Mar. 31, 2005

(65) Prior Publication Data
US 2005/0277189 A1    Dec. 15, 2005

Related U.S. Application Data

(60) Provisional application No. 60/557,870, filed on Mar. 31, 2004.

(51) Int. Cl.
C12N 5/07 (2010.01)
C12N 5/793 (2006.01)
C12N 5/797 (2006.01)

(52) U.S. Cl. .................... 435/325; 435/368; 435/373

(58) Field of Classification Search ............... 435/325, 435/368, 373
See application file for complete search history.

(56) References Cited

U.S. PATENT DOCUMENTS

| | | | |
|---|---|---|---|
| 6,468,794 B1 | 10/2002 | Uchida et al. | 435/368 |
| 6,638,763 B1 * | 10/2003 | Steindler et al. | 435/368 |
| 2002/0098584 A1 | 7/2002 | Palmer et al. | 435/366 |
| 2003/0095956 A1 | 5/2003 | Weiss et al. | 424/93.21 |
| 2003/0166276 A1 | 9/2003 | Carpenter | 435/368 |
| 2005/0037488 A1 * | 2/2005 | Mitalipova et al. | 435/366 |

OTHER PUBLICATIONS

Leventhal et al. 1999. Endothelial Trophic Support of Neuronal Production and Recruitment from the Adult Mammalian Subependymal zone. MCN. 13:450-464 (IDS reference-DB).*

Doetsch 2003. A niche for adult neural stem cells. Current Opinion in Genetics & Development. 13:543-550.*

Kirschenbaum et al., "Brain-derived neurotrophic factor promotes the survival of neurons arising from the adult rat forebrain subependymal zone," Proc. Natl. Acad. Sci. USA, 92, pp. 210-214 Jan. 1995.

Leventhal et al., "Endothelial Trophic Support of Neuronal Production and Recruitment from the Adult Mammalian Subependyma," Molecular and Cellular Neuroscience, 13, pp. 450-464 (1999).

Pagano et al., "Isolation and Characterization of Neural Stem Cells from the Adult Human Olfactory Bulb," Stem Cells, 18, pp. 295-300 (2000).

Palmer et al., "Vascular Niche for Adult Hippocampal Neurogenesis," Journal of Comparative Neurology, 425, pp. 479-494 (2000).

Qian et al., "Timing of CNS Cell Generation: A Programmed Sequence of Neuron and Glial Cell Production from Isolated Murine Cortical Stem Cells," Neuron, 28, pp. 69-80, Oct. 2000.

Takahashi et al., "Retinoic Acid and Neurotrophins Collaborate to Regulate Neurogenesis in Adult-Derived Neural Stem Cell Cultures," J. Neurobiol. 38(1), pp. 65-81, 1999.

Palmer et al., "Fibroblast Growth Factor-2 Activates a Latent Neurogenic Program in Neural Stem Cells from Diverse Regions of the Adult CNS," Journal of Neuroscience, 19(19), pp. 8487-8497 Oct. 1999.

Shimazaki et al., "The Ciliary Neurotrophic Factor/Leukemia Inhibitory Factor/gp130 Receptor Complex Operates in the Maintenance of Mammalian Forebrain Neural Stem Cells," Journal of Neuroscience, 21(19), pp. 7642-7653, Oct. 2001.

Zhu et al., "Vascular endothelial growth factor promotes proliferation of cortical neuron precursors by regulating E2F expression," The FASEB Journal, 17, pp. 186-193, Feb. 2003.

Tropepe et al., "Direct Neural Fate Specification from Embryonic Stem Cells: A Primitive Mammalian Neural Stem Cell Stage Acquired through a Default Mechanism," Neuron, 30, pp. 65-78, Apr. 2001.

Hitoshi et al., "Notch pathway molecules are essential for the maintenance, but not the generation, of mammalian neural stem cells," Genes & Development, 16, pp. 846-858 (2002).

Nacher et al., "NMDA receptor antagonist treatment increases the production of new neurons in the aged rat hippocampus," Neurobiology of Aging, 24, pp. 273-284 (2003).

Kempermann et al., "Early determination and long-term persistence of adult-generated new neurons in the hippocampus of mice," Development, 130, pp. 391-399 (2003).

Aberg et al., "Peripheral Infusion of IGF-I Selectively Induces Neurogenesis in the Adult Rat Hippocampus," Journal of Neuroscience, 20(8), pp. 2896-2903, Apr. 2000.

* cited by examiner

*Primary Examiner* — Taeyoon Kim
(74) *Attorney, Agent, or Firm* — Heslin Rothenberg Farley & Mesiti P.C.; Kathy Smith Dias

(57) ABSTRACT

The present invention provides a mechanism for obtaining an almost unlimited source of stem cells. A method for the expansion of a population of stem cells that retain their developmental capacity comprises co-culture of a stem cell population with a trophic support, for example, endothelial cells or conditioned medium derived from endothelial cell culture. The method also provides a method for enhancing neurogenesis when neural stem cells are co-cultured with the endothelial cell-derived trophic support to retain their neurogenic potential.

13 Claims, 27 Drawing Sheets

METHOD FOR STIMULATING SELF-RENEWAL OF NEURAL STEM CELLS AND ENHANCING NEUROGENESIS

CROSS-REFERENCE TO RELATED APPLICATIONS

This application claims priority from U.S. Ser. No. 60/557,870 filed Mar. 31, 2004, the disclosure of which is hereby incorporated by reference in its entirety.

STATEMENT OF RIGHTS UNDER FEDERALLY SPONSORED RESEARCH

This invention was made with government support under grant number R37 NS033529-09 awarded by the NINDS of the National Institutes of Health. The government has certain rights in the invention.

FIELD OF THE INVENTION

The present invention generally relates to a method for promoting self-renewal of neural stem cells and enhancing neurogenesis. More significantly, the invention provides a method for the proliferation of a stem cell population that retains its developmental capacity to differentiate into a specific cell type.

BACKGROUND OF THE INVENTION

During embryogenesis, the developmental potential of individual cells is continuously restricted. During CNS development, neurogenesis largely precedes gliogenesis. Isolated stem cells from the embryonic mouse cerebral cortex, for example, exhibit a distinct order of cell-type production: neuroblasts first and glioblasts later. This is accompanied by changes in their capacity to make neurons versus glia. Thus, multipotent stem cells alter their properties over time and undergo distinct phases of development that play a key role in scheduling production of diverse CNS cells.

Current methods of culturing neural stem cells result in poor self-renewal and limited neuron production, particularly projection neurons. What is needed is a culture system that could provide an almost unlimited source of neural stem cells having a specific developmental capacity for cell-replacement strategies.

Stem cell expansion and differentiation are regulated in vivo by environmental factors encountered in the stem cell niche (1). In the adult, neural stem cells lie close to blood vessels: in the hippocampus (2), the subventricular zone (SVZ) (3), and the songbird higher vocal center (4). In the developing central nervous system (CNS), ventricular zone cells produce vascular endothelial growth factor (VEGF), which attracts vessel growth towards them (5). Thus, vascular cells are close to CNS germinal zones throughout life, and it has been suggested that they form a niche for neural stem cells (2).

SUMMARY OF THE INVENTION

In one aspect, the invention relates to a method for expanding a population of stem cells that retain their capacity to differentiate into neurons, the method comprising the steps of obtaining an original population of stem cells having a particular developmental capacity and culturing the stem cells in the presence of a trophic support, such as vascular endothelial cells or a conditioned media from a vascular endothelial cell culture, in an amount sufficient to stimulate self-renewal of the stem cells. The endothelial cells may be cultured non-contiguously from the stem cell population, that is, not in contact but allowing for soluble factors produced by the endothelial cells to come into contact with the stem cells. The resulting expanded population of stem cells retains the developmental capacity of the stem cells.

In one aspect of the invention the stem cells are embryonic stem cells. The endothelial cells may be derived from a primary culture or may be a cell line. In one embodiment of the invention, the endothelial cells are pulmonary artery endothelial cells. In an alternate embodiment, the endothelial cells are derived from brain tissue.

In another aspect, the invention relates to a method for promoting the self-renewal of neural stem cells and enhancing neurogenesis. The method promotes both proliferation of the neural stem cells and more importantly, retention of their developmental capacity to differentiate into neurons. A method for enhancing neurogenesis comprises the steps of 1) obtaining a population of neural stem cells having a developmental capacity to differentiate into neurons; 2) culturing the stem cells in the presence of a trophic support selected from the group consisting of a) vascular endothelial cells and b) conditioned media from a vascular endothelial cell culture, in an amount sufficient to stimulate self-renewal of the neural stem cells. The method comprises the further step of removing the trophic support after expansion of the population has been achieved, so that the expanded population of neural stem cells can differentiate into neurons, including projection neurons as well as interneurons.

DETAILED DESCRIPTION OF THE INVENTION

All patents, applications, publications and other references listed herein are hereby incorporated by reference in their entirety. In the description that follows, certain conventions will be followed as regards the usage of terminology.

The term "stem cell" as it is known and used in the art refers to an undifferentiated cell having the ability to proliferate and self-renew and ultimately being able to differentiate into a specific cell type, for example, a neuron.

The term "neural stem cell" refers to an undifferentiated cell derived from the nervous system having the ability to proliferate and self-renew and ultimately being able to differentiate into a one of the cells of the nervous system, for example, a neuron.

The term "trophic support" refers to a source of exogenous trophic factors and includes without limitation, a cell co-culture which secretes trophic factors, a conditioned medium obtained from a cell culture that secretes trophic factors or a cocktail of purified trophic factors.

Neural stem cells can be used for transplantation into a heterologous, autologous or xenogeneic host. Neural stem cells are isolated from nervous system tissue in accordance with methods known to those of skill in the art and may be obtained from embryonic, post-natal, juvenile or adult neural tissue from human or non-human mammals. The desired resulting cell type, for example, neurons, will determine the developmental stage of the tissue from which the stem cells will be isolated. So for example, to enhance the number of neurons obtained from an expanded stem cell population, the stem cells to be expanded will be obtained from tissue that is at the optimal developmental stage for neuronal differentiation (for example, E10-11 in the mouse.)

The stem cells are then co-cultured with endothelial cells or are cultured in a conditioned medium obtained from an endothelial cell culture. Cells may be passaged indefinitely or stored frozen in accordance with methods known in the art.

Figure 1A:
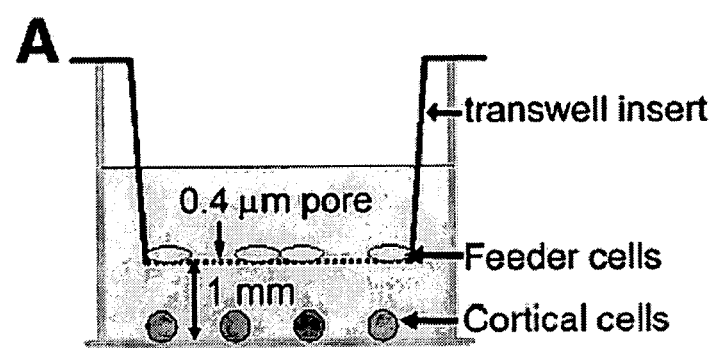
FIG. 1A is a schematic representation of one embodiment of a co-culture system employed in practicing the method of the present invention.
Figure 1B:
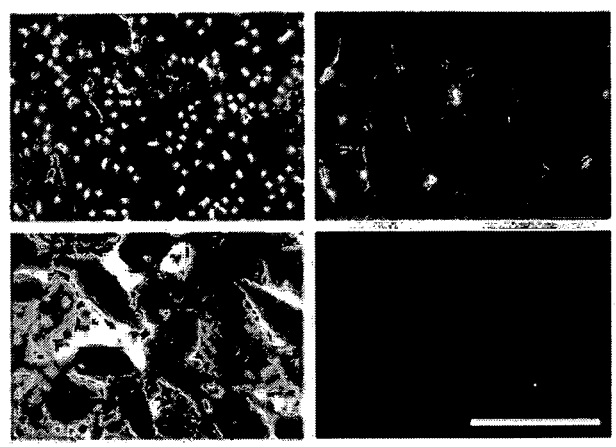
FIGS. 1B-D. are photomicrographs illustrating the effect of co-culture of cortical stem cells with endothelial cells as compared to co-culture with cortical cells.
Figure 1C:
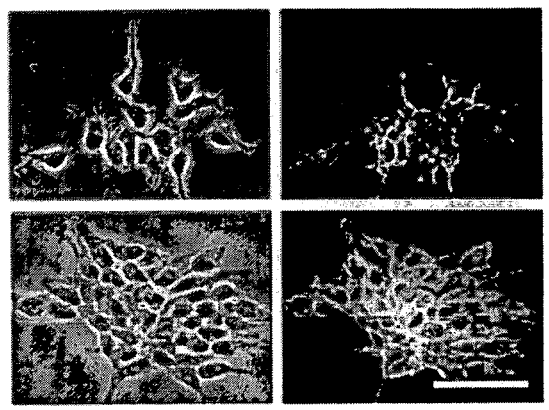
Figure 1D:
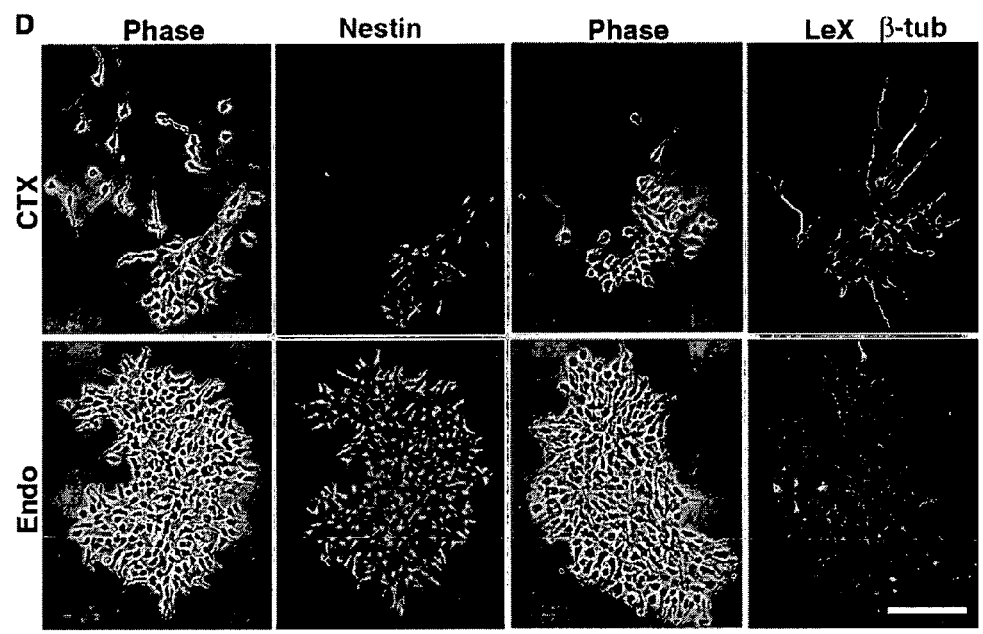
Figure 1E:
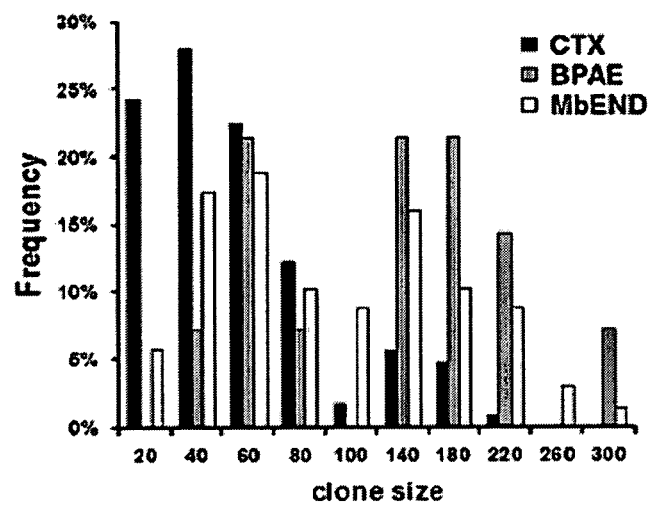
FIGS. 1E-G are bar graphs showing the effect of endothelial cell co-culture on clone size, frequency of larger clones and percentage of neural progenitor cells.
Figure 1F:
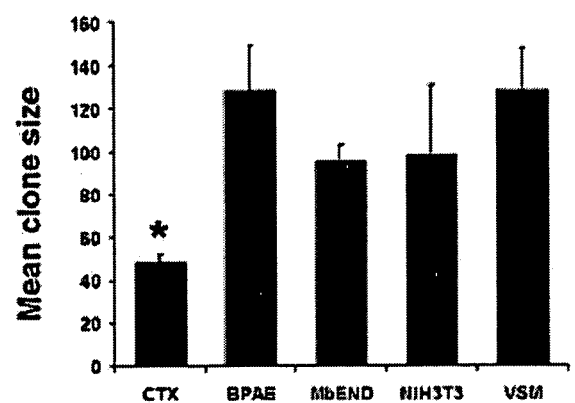
Figure 1G:
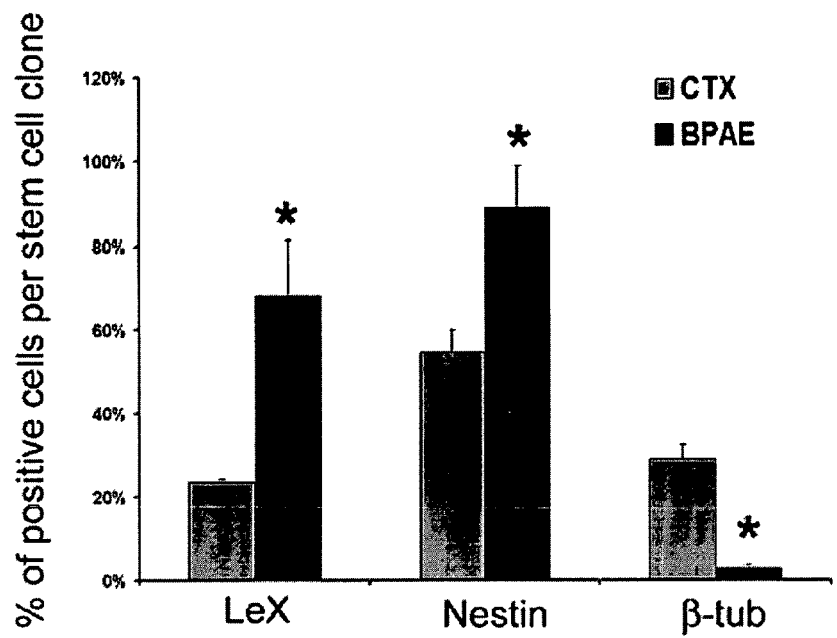

To examine a possible functional interaction between neural stem cells and their vascular environment, we co-cultured neural and vascular cells (FIG. 1A). Neural stem cells from E10-11 mouse cerebral cortex were plated at clonal density on the base of culture wells, while the upper compartment, formed by the insertion of a TRANSWELL® permeable membrane insert into the well, was seeded with purified vascular-associated or other feeder cells: primary bovine pulmonary artery endothelial cells (BPAE), a mouse brain endothelial cell line (MbEND), vascular smooth muscle (VSM) cells, NIH3T3 fibroblasts, or as a control, high density, age-matched cortical cells (CTX). FIG. 1B shows that CD31 stains endothelial cells in the permeable membrane inserts (upper panel), but no CD31$^+$ cells are detected below in the cortical cell compartment (lower panel). Thus, CD31$^+$ (PE-CAM) endothelial cells were never found in the lower compartment when BPAE or MbEND cells were plated in the upper compartment, confirming that the feeder cells cannot migrate through the 0.4 μm diameter membrane pores.

As expected (6), embryonic stem cell clones co-cultured with CTX began producing neurons within a day. Most neuron production was over by 7 days, and growth after this time was largely in glial lineages. Clones co-cultured with BPAE or MbEND cells behaved differently (FIG. 1D), growing into sheets of largely flattened progeny that maintained tight cell-cell contact, illustrated by strong junctional β-catenin staining (FIG. 1C), with only a few immature, neuron-like cells appearing on top of the sheets. Neural stem cell clones grown with endothelial cells were larger, with more primitive progeny (expressing the progenitor markers Nestin and LeX (20), and fewer neurons (expressing β-tubulin-III) than were clones grown with CTX (FIG. 1 D-G). Hence, endothelial factors facilitate expansion of cortical stem cell clones and inhibit their differentiation. VSM and NIH3T3 cells also promoted neural stem cell proliferation (FIG. 1F), but clones were less cohesive and included more glial-like progeny than those in endothelial co-culture.

Figure 2A:
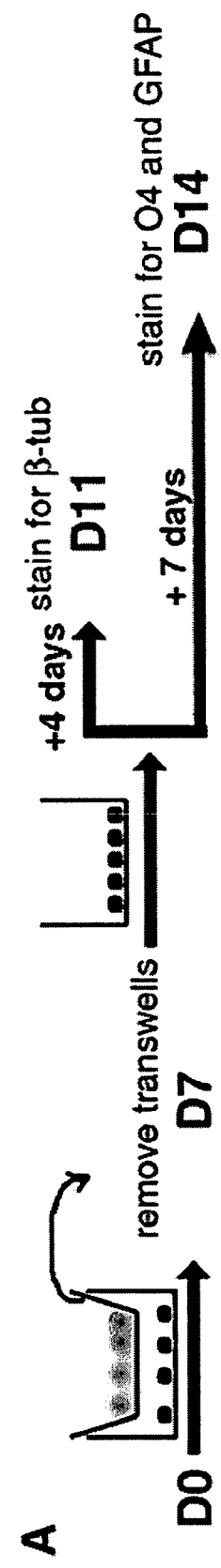
FIG. 2A is a schematic representation of removal of trophic support from the co-culture system to allow differentiation of stem cells.
Figure 2B:
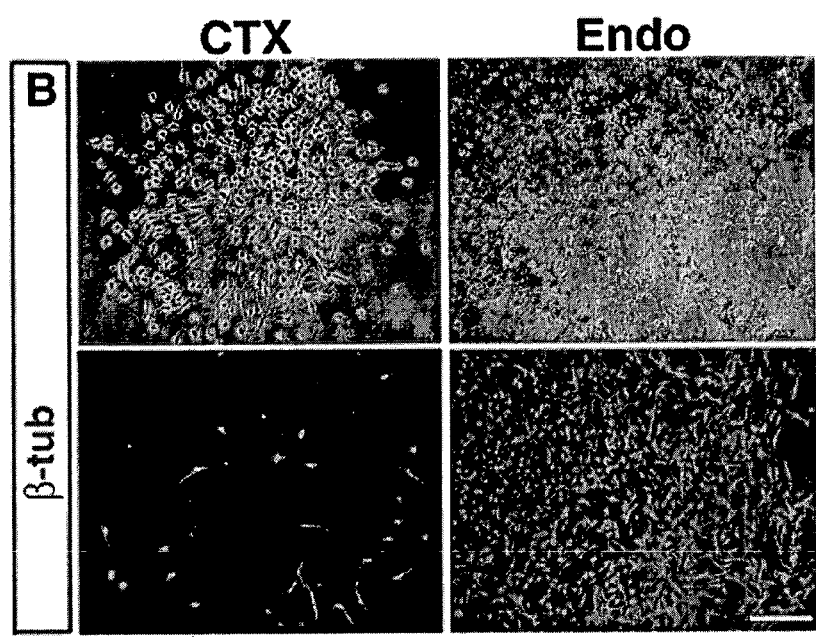
FIGS. 2B-G show the effect on various parameters of E10-11 cortical stem cells co-cultured with endothelial cells (Endo) vs. co-culture with cortical cells (CTX).
Figure 2C:
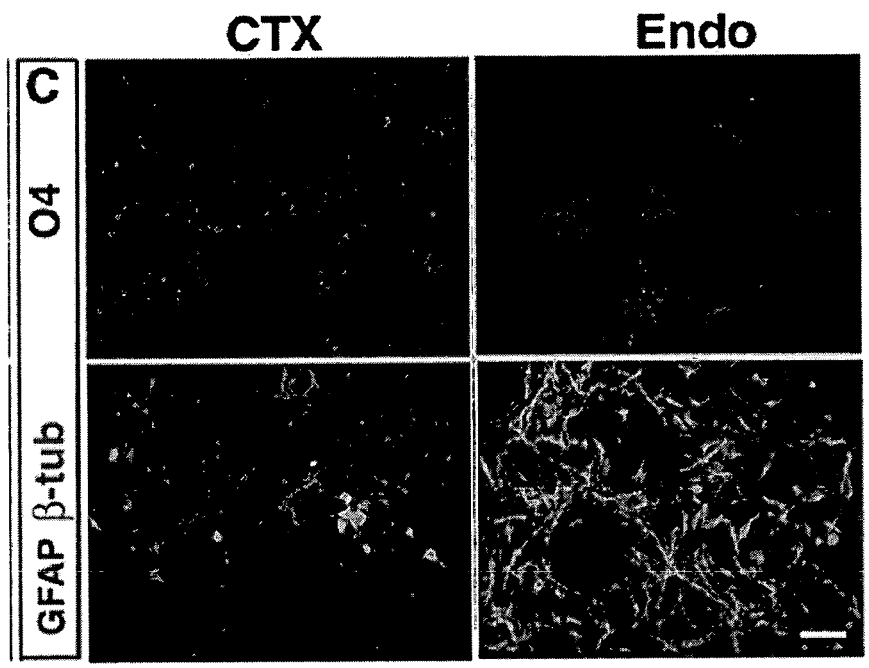
Figure 2D:
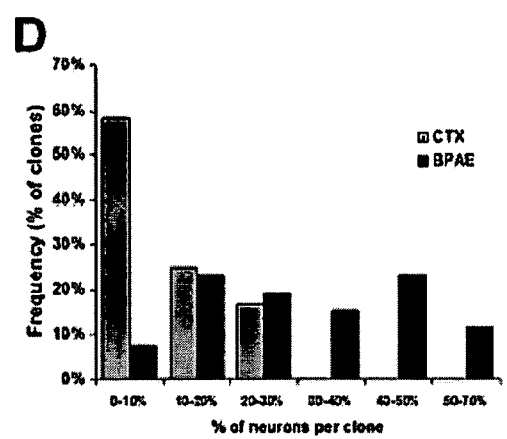
Figure 2E:
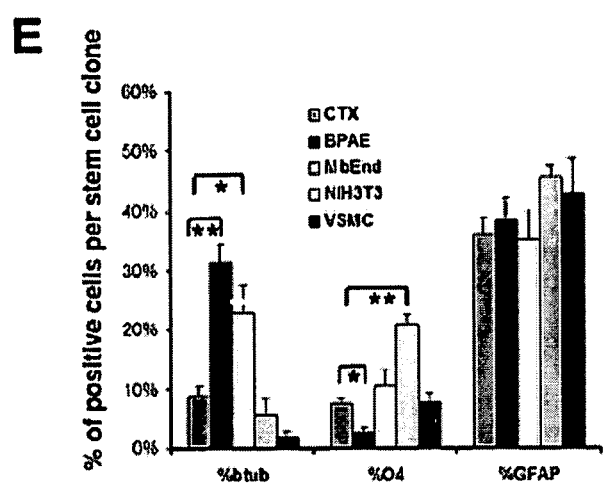

When the permeable membrane inserts were removed, endothelial-expanded stem cell clones continued to proliferate but also began to differentiate, and within 4 days produced β-tubulin-III$^+$ neurons (FIG. 2B), which were almost all MAP-2$^+$. Approximately 30% of the neurons had acquired the later neuronal marker NeuN (data not shown). The clones contained up to approximately 10,000 progeny, and on average 31% were neurons. In contrast, in control CTX co-cultures 4 days after removal of the permeable membrane inserts, stem cell clones ranged up to 4350 cells, and on average only 9% were neurons; similarly, E11 cortical cells cultured as neurospheres for 7 days then differentiated in adherent culture for 4 days produced only 7% neurons. Many more stem cell clones growing in BPAE co-cultures contained a higher percentage of neurons, up to 64%, compared to CTX co-culture (FIG. 2D, E), and neuron production was prolonged. Increased neurogenesis from endothelial co-cultured neural stem cells does not occur at the expense of gliogenesis: the percentage of GFAP$^+$ astrocytes generated was similar, and although oligodendrocyte differentiation (indicated by O4 staining) was reduced in BPAE co-cultures compared to CTX, the difference could not account for the enhancement of neuron generation (FIG. 2C, E). NIH3T3 cells enhanced oligodendrocyte generation. Co-culture with VSM or NIH3T3 cells reduced neurogenesis compared to CTX (FIG. 2E), showing that the endothelial effect is cell-type specific.

Figure 2F:
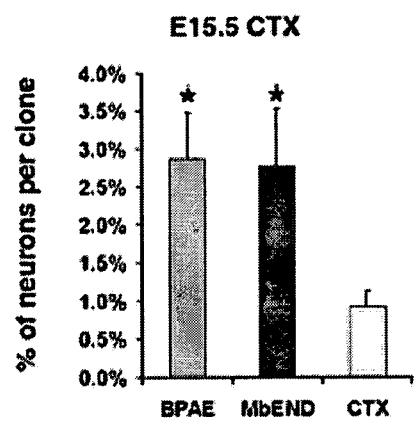
Figure 2G:
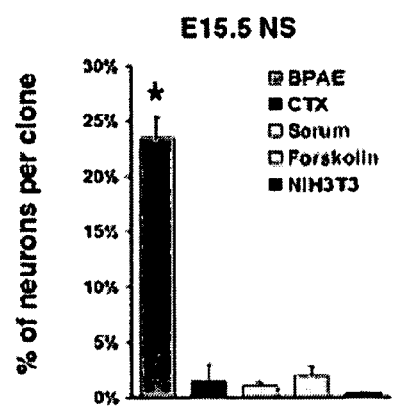
Figure 2H:
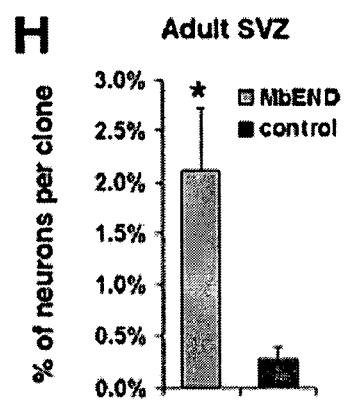

Endothelial cells stimulate proliferation and neurogenesis of neural stem cells from a variety of embryonic CNS regions (not shown) and from different stages. E15.5 cortical and adult SVZ stem cells grown in endothelial co-culture generated sheets of LeX$^+$, Nestin$^+$ cells. After differentiation, E15.5 endothelial-expanded cortical cells and adult SVZ cells produce more neurons compared to control (FIG. 2F, 2H).

Neurosphere-expanded stem cells respond to endothelial factors. E15.5 cortical cells grown as neurospheres in FGF2 for 7 days were plated in adherent conditions and co-cultured for 3 days with endothelial cells or with age-matched cortical cells, then differentiated by withdrawing feeder cells for 4 days. Stem cells exposed to endothelial factors produced 22% neurons, compared to 2% neurons in control CTX co-cultures (FIG. 2G).

Figure 3A:
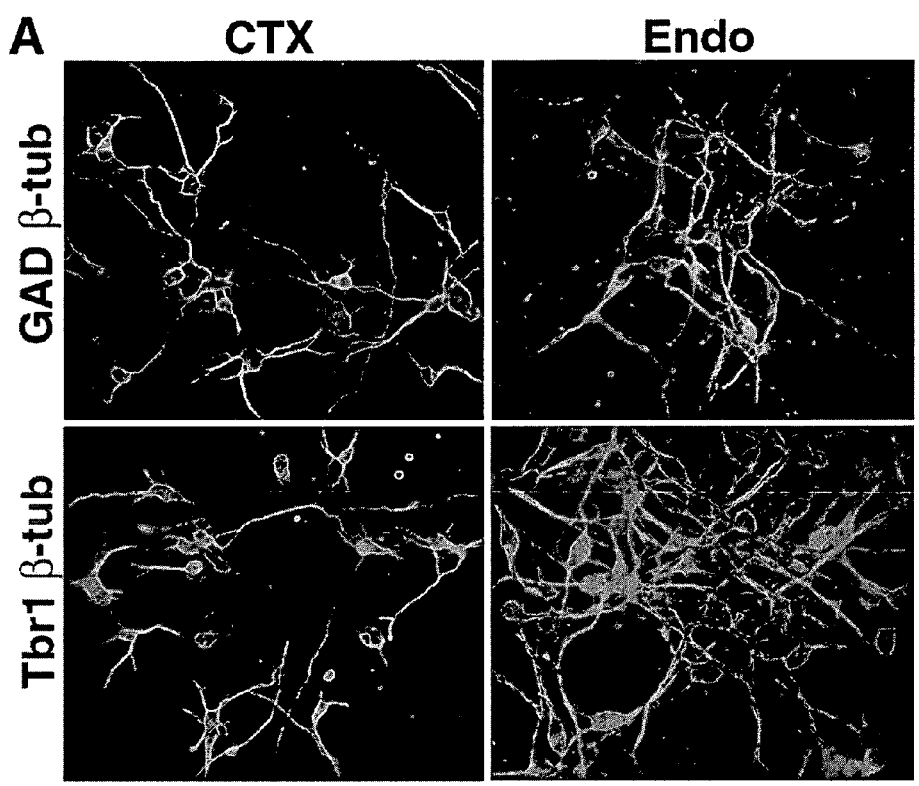
FIG. 3A are photomicrographs showing the distribution of GAD (cytoplasmic marker), Tbr1 (nuclear marker) and β-tubulin-III in endothelial expanded E10 stem cell clones.
Figure 3B:
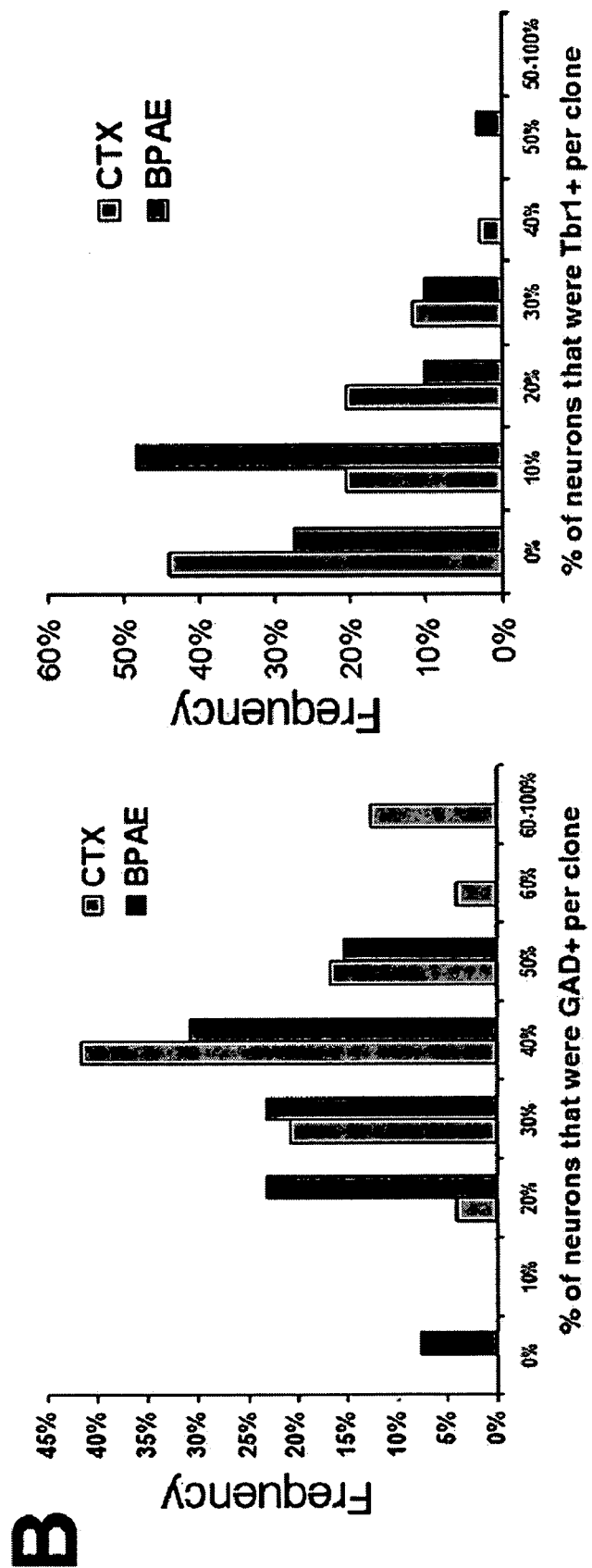
FIG. 3B contains histograms showing frequency of $GAD^+$ and $Tbr1^+$ neurons in stem cell clones.

In vivo, most projection neurons are born in the early embryonic period, while glia and interneurons arise later; adult stem cells are primed to generate interneurons (24,25). To examine the neuron sub-types generated from E10-11 cortical stem cells expanded in endothelial co-culture, differentiated clones were stained for GAD67, a GABAergic marker typically expressed in interneurons, or Tbr1, an early pyramidal neuron marker that preferentially labels projection neurons (26) (FIG. 3A). More stem cell clones growing in BPAE co-culture made Tbr1$^+$ projection neurons, compared to CTX co-culture (FIG. 3B) or to neurosphere-expanded E10 cells that were subsequently differentiated in adherent culture (9.95% versus 2.41%). Thus, endothelial cell co-culture supports development of both projection neurons and interneurons.

That projection neurons typical of the early embryo arise in E10-11 co-cultures after many cell divisions suggests that endothelial factors promote stem cell self-renewal, and inhibit the normal progression in which older stem cells preferentially produce glia or interneurons. We found few Tbr1+ neurons produced from E15.5 stem cells and none from adult SVZ cells, indicating that endothelial factors are permissive, not instructive, for this fate: they cannot reverse the restriction.

Figure 4A:
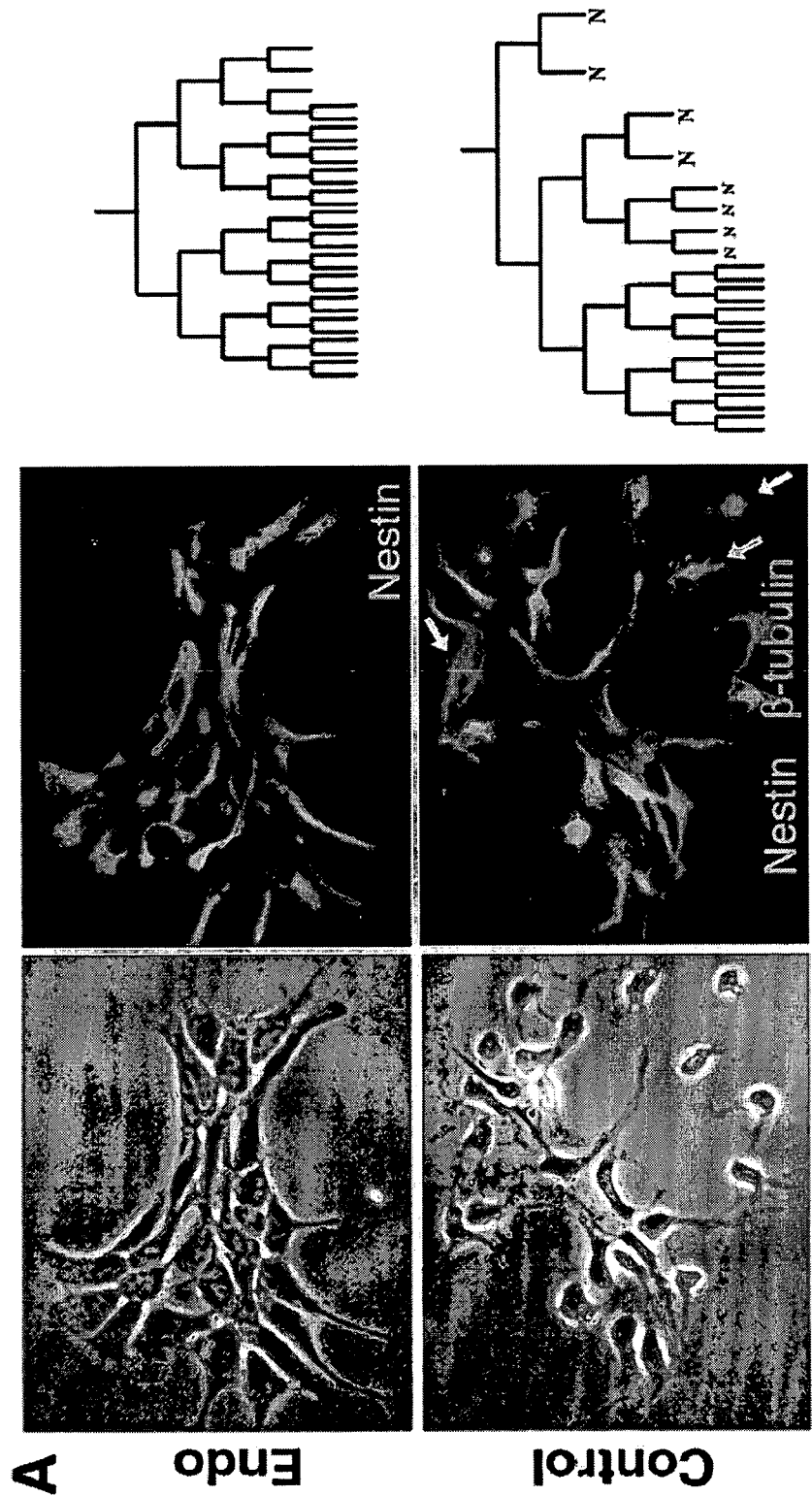
FIG. 4A is a comparison between typical lineage trees reconstructed from time-lapse video recordings of single E10 cortical stem cells grown with endothelial cells (Endo), and those grown in control conditions.

Supporting the hypothesis that endothelial factors promote stem cell self-renewal, time-lapse video recording of dividing clones reveals that stem cells grown with endothelial cells undergo symmetric, proliferative divisions generating Nestin$^+$ progeny, in contrast to the asymmetric division patterns seen in control conditions (23,27) (FIG. 4A). Cortical stem cells co-cultured with endothelial cells for 4 days generated more secondary stem cell clones, neurospheres and neuron-generating progenitor cells than did those co-cultured with CTX cells.

Figure 4B:
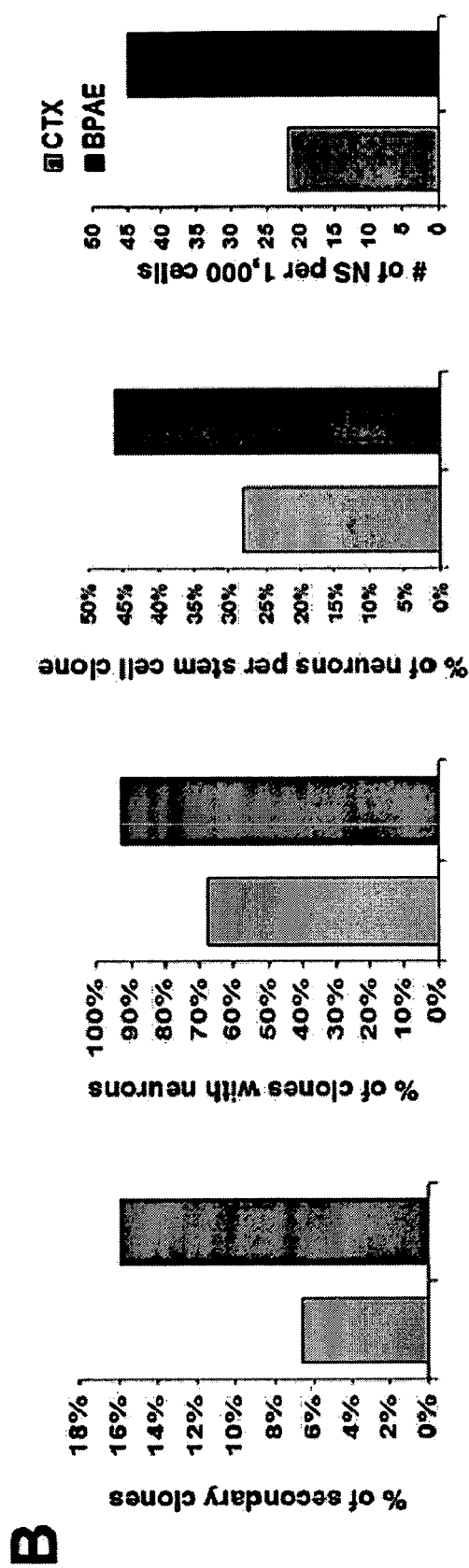
FIG. 4B is a graph showing that β-catenin staining is significantly decreased and β-tubulin-III staining is significantly increased in BPAE co-culture clones that were treated with γ-secretase inhibitor II for 6 hours.
Figure 4C:
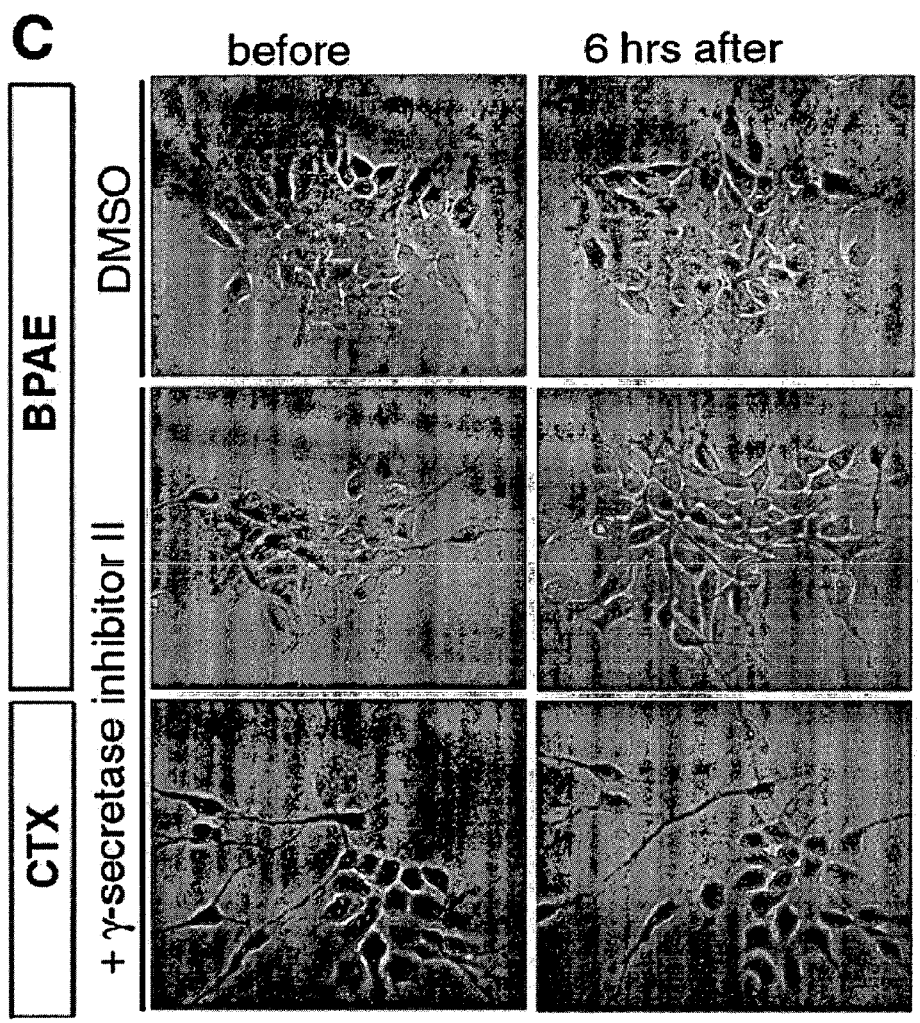
FIG. 4C is an RT-PCR gel showing that endothelial cell co-culture stimulates Notch and Hes1 activity.
Figure 4D:
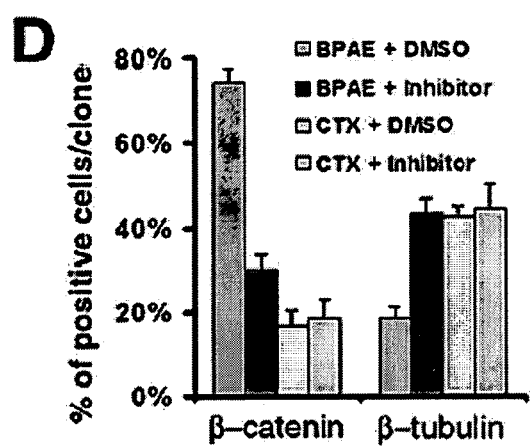
Figure 4E:
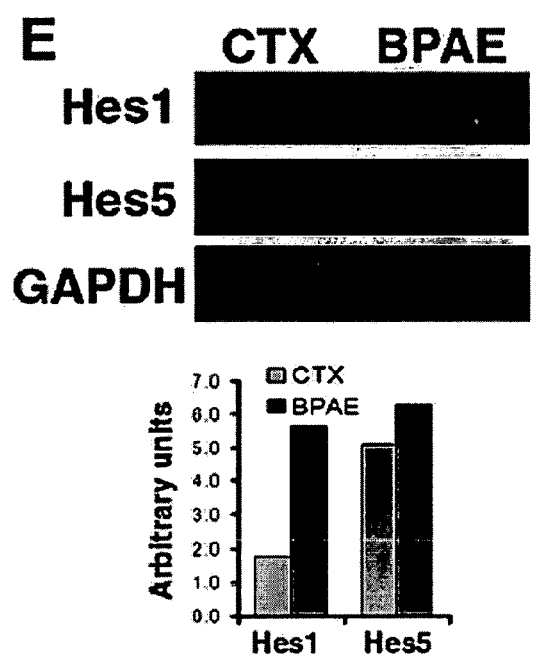
Figure 5:
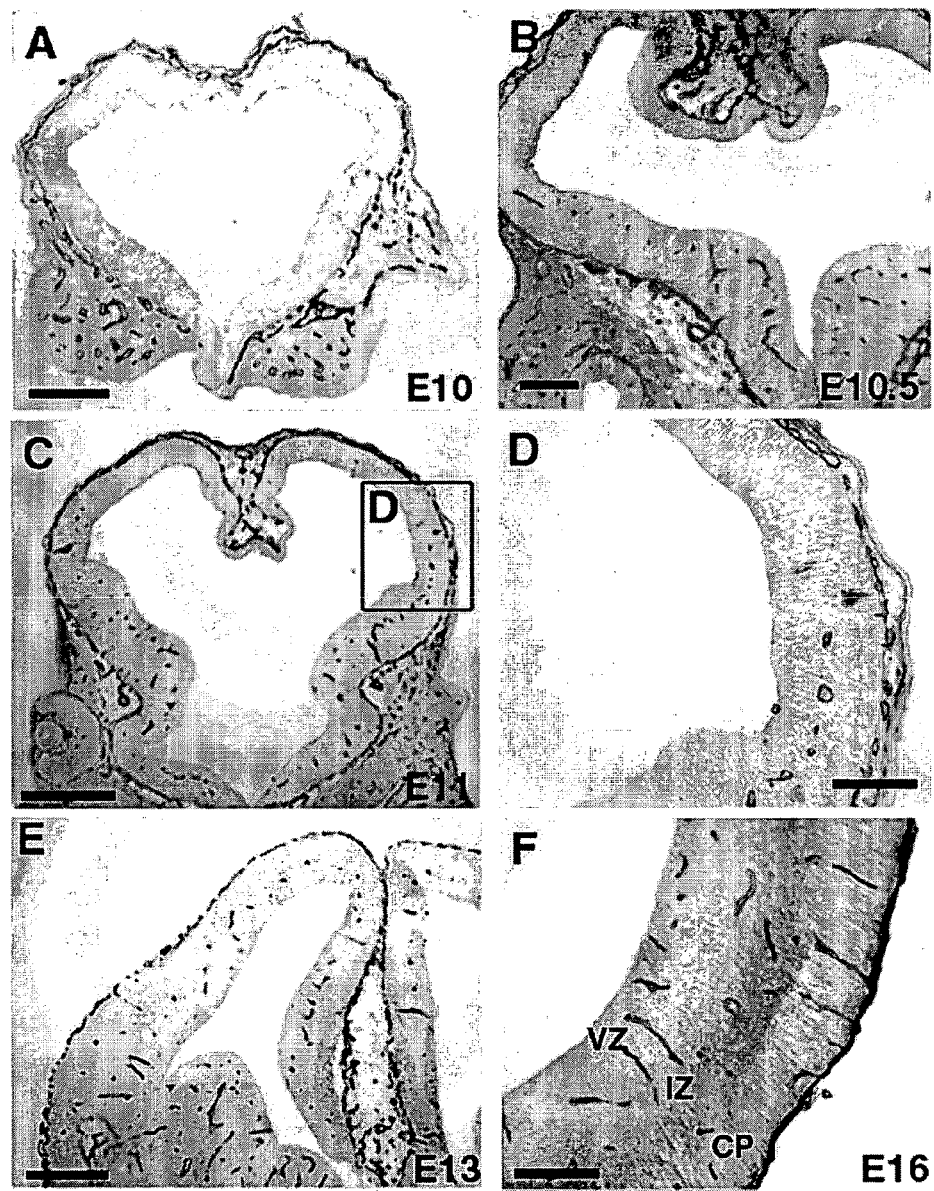
FIG. 5 are histological sections showing that $CD31^+$ endothelial cells are prominent in germinal zones in the developing telencephalon.
Figure 6:
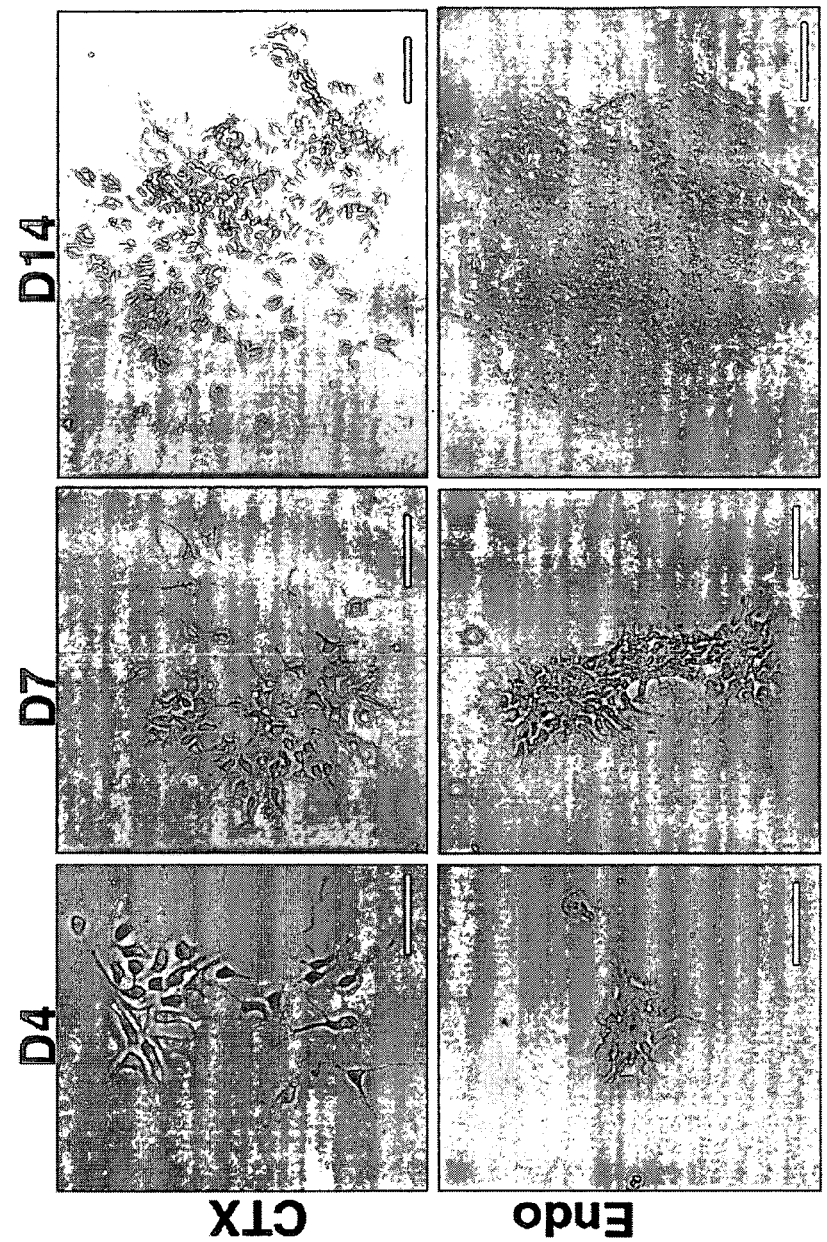
FIG. 6 is a comparison of clonal growth when E10-E11 cortical cells are co-cultured with endothelial cells or cortical cells.

The most obvious effect of endothelial factors is that they promote neural stem cell growth as epithelial sheets with extensive junctional contacts (FIG. 1C), which could promote self-renewal by influencing β-catenin signaling pathways (28,29), mode of cell division (30), and maintaining Notch activation (31). Indeed, stem cells co-cultured with endothelial cells and then exposed to γ-secretase inhibitor II, which inhibits Notch1 activation (32), showed similar extent of cell-cell contact, division and differentiation to those in CTX co-cultures (FIG. 4B). In neural stem cells cultured with endothelial factors the Notch effector Hes1 was up-regulated but Hes5 was not (FIG. 4C), consistent with involvement of Hes1 in neural stem cell self-renewal (33, 34).

Our results identify endothelial cells as critical components of the neural stem cell niche, as they secrete soluble factors that maintain CNS stem cell self-renewal and neurogenic potential. Thus, while FGF2 promotes neural stem cell proliferation, it cannot alone maintain their self-renewal; endothelial factors acting with FGF2 accomplish this.

In the presence of endothelial cells, a neural stem cell undergoes symmetric, proliferative divisions to produce undifferentiated stem cell sheets that maintain their multipotency and upon endothelial cell removal generate neurons as well as astrocytes and oligodendrocytes. No CD31$^+$ cells were detected in clones, showing that, at least under these circumstances, neural stem cells do not generate endothelial progeny.

Growth with endothelial cell-derived factors may be an important tool for promoting neural stem cell self-renewal and neurogenesis, allowing efficient production of neural stem cells and a variety of CNS neurons for use in replacement therapies.

Cell Culture

Embryonic cerebral cortices and adult SVZ were dissected and dissociated as described (18-20). Single cells were plated into poly-l-lysine-coated 6-well plates (Costar) at clonal density (2000-4000 cells/well) and cultured in basal serum-free medium consisting of DMEM, B27, N2, NAC and 10 ng/ml FGF2 (19,20). To test the effects of soluble growth factors (PDGF, CNTF, TGFβ, IGF1, IL1, IL6, G-CSF, M-CSF, GM-CSF, LIF, BDNF, Steel factor, VEGF or EGF), each factor was added to serum-free medium with FGF2 at a range of 10-50 ng/ml, and clonal growth (cell number and generation of neurons and glia) was assessed (without co-cultured feeder cells). LIF and VEGF were also tested in combination, each added at 10 ng/ml into serum-free medium, with and without FGF2.

For co-culture experiments, bovine pulmonary artery endothelial (BPAE) cells (VEC Technologies INC., ATCC, #CCL-209) or mouse brain endothelial cells (ATCC, #CRL-2299)(4) were used at passage 14-16. Three days before co-culturing with cortical cells, endothelial cells were plated into 24 mm TRANSWELL® permeable membrane inserts (Costar) at 2000 cells/well, in DMEM with 10% FBS. Four hours before use, the inserts were well rinsed and transferred to serum-free medium containing 10 ng/ml FGF2. For control conditions, NIH3T3 fibroblasts, vascular smooth muscle (VSM) cells or cortical cells were plated in the inserts at the same density and grown in the same manner as endothelial cells.

The inserts were placed above freshly plated neural stem cells, and the cultures fed every two days with serum free medium. To differentiate the clones, the inserts were removed and the cells cultured for 4 or 7 days, in some experiments with removal of FGF2 and/or addition of 1% FBS, 5 μM forskolin, or 1 μM retinoic acid.

Adult forebrain SVZ stem cells were grown in adherent culture with endothelial co-culture for 7 days, and for a further 7 days after removal of the inserts.

Neurosphere Culture and Differentiation

Cortical cells were plated at a density of 2000 cells/well into non-coated 6-well plates in DMEM, B27, N2, NAC and 20 ng/ml FGF for 7 days to generate neurospheres.

E10-E11 neurospheres were transferred to PLL-coated plates in medium without mitogen and cultured for 7 days before fixation and staining for β-tubulin-III and Tbr1. The percentages of β-tubulin-III$^+$ neurons per neurosphere and of Tbr1$^+$ neurons were calculated for comparison with endothelial co-cultured adherent E10-E11 cortical stem cell clones.

E15.5 neurospheres were transferred to PLL-coated 6-well plates and co-cultured with BPAE, CTX or NIH3T3 feeder cells in permeable membrane inserts for 3 days, or without feeder cells but with added 1% FBS, or 5 μM forskolin. Differentiation of feeder co-cultures was stimulated by removal of inserts and growth factors for a further 4 days. Cultures were then fixed and stained for β-tubulin-III.

Sub-Cloning to Analyse Self-Renewal and Neurogenic Potential of Stem Cell Clones E10-11 cortical stem cells were cultured for 4 days in either endothelial or CTX co-culture then removed from the wells using trypsin. A sample of each single cell suspension was plated into non-adherent conditions at 1000 cells/well in 6-well plates and allowed to grow into neurospheres that were counted after 7 days in vitro. The remaining single cells were replated at clonal density in PLL-coated 6-well plates in serum-free medium with 10 ng/ml FGF2 and allowed to grow for 5 days. The clones were then fixed and stained, and total progeny and number of β-tubulin-III$^+$ neuronal progeny were calculated.

Long-Term Time-Lapse Microscopy

Time-lapse video images (18) of E10 cortical clones were recorded for 3-4 days, then the clones were fixed and stained for Nestin and β-tubulin-III. Lineage trees were reconstructed from the recorded cell divisions. The appearance of identified individual progeny was mapped within the lineage trees. This showed the birth of neurons and progenitor cells during clonal development.

Immunostaining

Cells were fixed in 4% paraformaldehyde in 0.1M PBS. Primary antibodies were used at the following concentrations: Nestin, 1:4 (Development Studies Hybridoma Bank); LeX, 1:20 (Becton Dickinson, CD15); β-catenin, 1:200 (Becton Dickinson); β-tubulin-III, 1:500 (Sigma); O4, 1:2 (Development Studies Hybridoma Bank), or 1:100 (Chemicon); GFAP, 1:400 (DAKO); GAD67, 1:2000 (Chemicon); Tbr1, 1:100 (a gift from Dr. Yi-Ping Hseuh). Secondary antibodies (Alexa fluoro-conjugated, Molecular Probes) were used at 1:250, and incubated for 45 minutes at room temperature.

BrdU Incorporation

Cortical stem cells were co-cultured with endothelial cells or cortical cells for 9 days. 10 μg/ml BrdU was added to the wells for 24 hours and then washed out. The permeable membrane inserts were removed and the underlying cortical cells were cultured for 2 more days, then fixed. Cells were stained for β-tubulin-III and BrdU (1:10, Becton-Dickinson).

Inhibition of Notch Activation

γ-secretase inhibitor II (Calbiochem, 50 μM) in DMSO was added to co-cultured cells after 4 days for 6 hours. The same amount of DMSO was used as vehicle control. The cells were then fixed and stained for β-tubulin III and double-labelled for Nestin or β-catenin, and the stained cells were quantified.

RT-PCR

Total RNA was isolated from E10.5 cortical cells co-cultured with BPAE cells or cortical cells for 4 days using RNeasy Mini Kit (Qiagen) according to manufacturer's instructions. Analysis of gene expression was done using semi-quantitative RT-PCR using SuperScript one-step RT-PCR with Platinum Taq (Invitrogen). The following primers were used:

Hes1—TCAACACGACACCGGACAAACC (SEQ ID NO.: 1) and
GGTACTTCCCCAACACGCTCGC (SEQ ID NO.:2);
Hes5—AAGTACCGTGGCGGTGGAGAT (SEQ ID NO.: 3) and GAGTAACCCTCGCTGTAGTCC (SEQ ID NO.: 4) (5); GAPDH—ATGTTTGTGATGGGTGTGAA (SEQ ID NO.:5) and
TGGGAGTTGCTGTTGAAGTC (SEQ ID NO.:6). PCR conditions were 94° C. 15 seconds, 57° C. 30 seconds, 72° C. 30 seconds; 24 cycles for Hes1 and Hes5, 18 cycles for GAPDH. RT-PCR gel band densities were calculated using ImageQuant software.

BrdU uptake reveals prolonged neurogenesis from neural stem cells in endothelial versus control co-cultures.

Figure 7A:
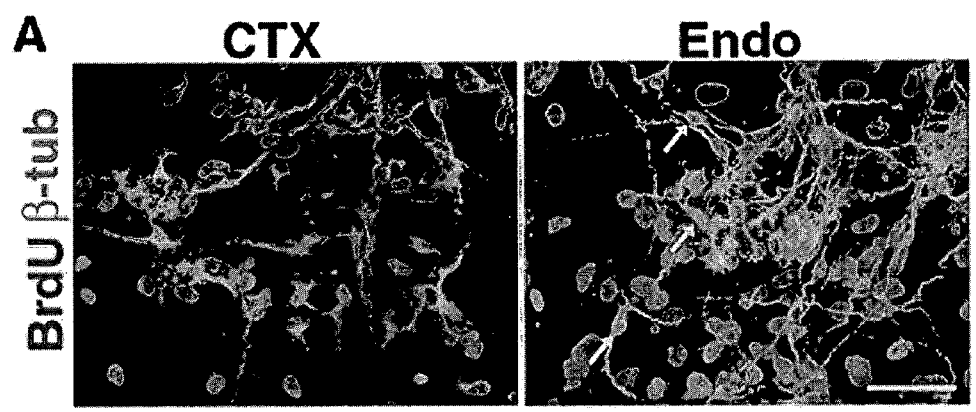
FIG. 7A shows the results of a double staining technique using BrdU and β-tubulin-III in endothelial vs. cortical cell-cocultures.
Figure 7B:
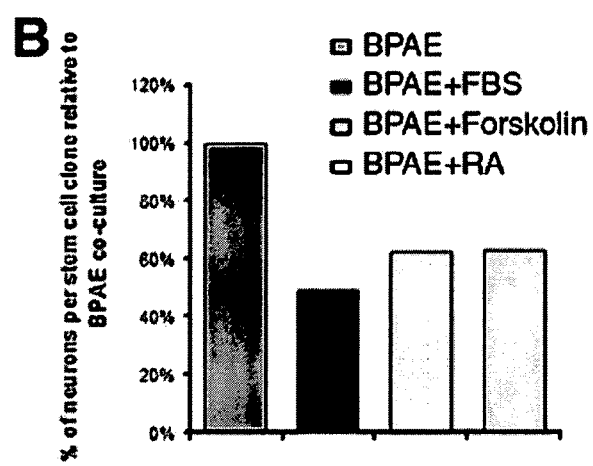
FIG. 7B is a bar graph showing the effect of the addition of serum, forskolin or retinoic acid on neuron production of E10-11 cortical stem cells grown with endothelial feeder cells. B. The percentage neurons per E15.5 cortical neurosphere after differentiation with addition of serum or forskolin.
Figure 8:
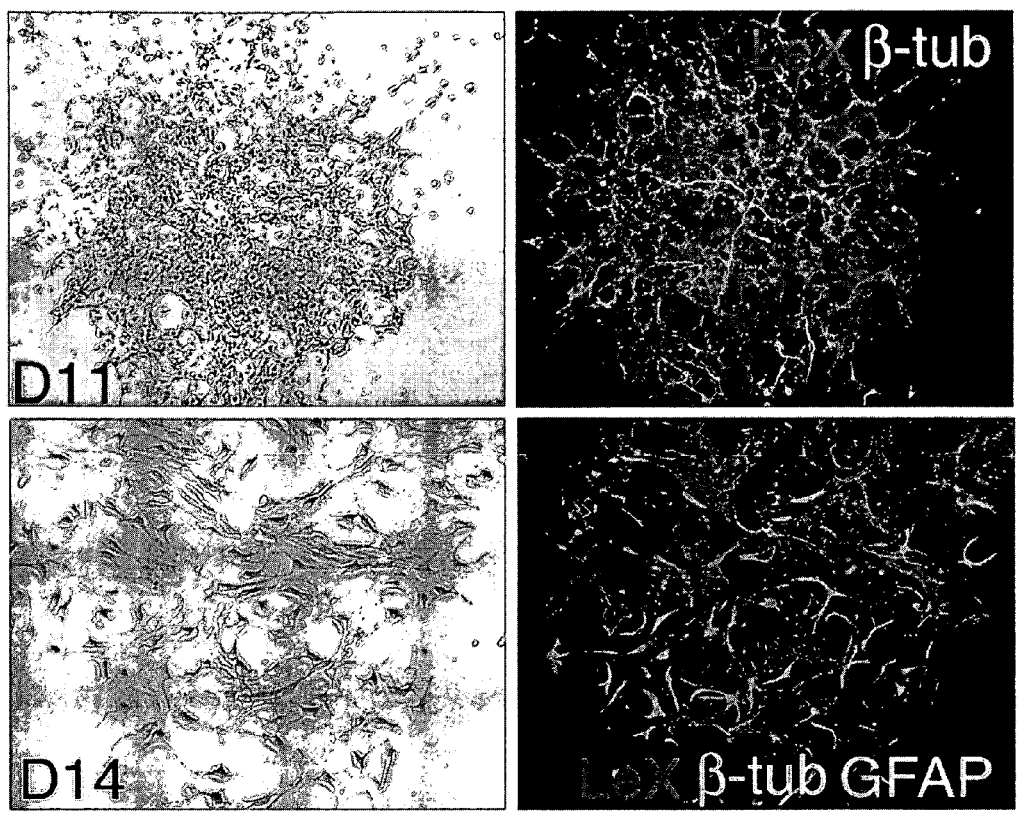
FIG. 8 are photomicrographs showing the effect of LIF and VEGF on stem cell culture.

Mouse cortical neurogenesis lasts about 7 days (from E11-E18) and is followed by gliogenesis (23). E10 cortical stem cells grown in FGF2 in vitro behave similarly (19). In contrast, neurogenesis is prolonged in endothelial versus CTX co-cultures, as shown by addition of BrdU at 9 days in vitro (FIG. 7A): neurons continue to be generated from dividing progenitors many days after tissue isolation (rather than simply differentiating from progenitors that had divided earlier).

Endothelial factors significantly enhanced self-renewal and neurogenesis compared to other added soluble factors.

While retinoic acid, FBS and forskolin can stimulate neuron production from some cell types (24-27), they actually depressed neurogenesis from E10-E11 cortical stem cells expanded in the presence of endothelial cells. Similarly, Eb15.5 neurosphere cells plated in adherent condition produced significantly more neurons (22%) when exposed to endothelial cell factors compared to serum or forskolin (FIG. 2G). Growth on fibronectin had little effect on neurogenesis (not shown), and the cortical progenitor cells did not grow well on Matrigel (not shown), underscoring the significant effect of endothelial-derived factors.

The fact that no contact is required between cortical cells and endothelial cells shows that soluble factors are responsible, and similar results were observed using endothelial cell-conditioned medium. Phase contrast photomicrographs showing stem cells grown in control culture medium in contrast to those grown in endothelial cell-conditioned medium and that have been stained for the progenitor marker, LeX showed that conditioned medium from endothelial cells supports growth of flattened sheets of mouse neural stem cells that retain expression of LeX (data not shown).

Endothelial cells secrete numerous bioactive substances. A compilation (28) includes 26 factors that are known to affect other cell types. Of these, we have tested PDGF, CNTF, FGF2, TGFβ, IGF1, IL1, IL6, G-CSF, M-CSF, GM-CSF, LIF, BDNF and Steel factor, and in addition EGF; none duplicated the result we see from endothelial co-cultures (data not shown). VEGF, which can be secreted by growing endothelial cells (29), and is expressed in developing and mature cerebral cortex microvessels (30), and LIF have both been reported to promote growth of neural progenitor cells (31-34). Neither factor, alone or in combination, duplicated the effect of endothelial factors: LeX expression was increased in cortical stem cell clones grown with 10 ng/ml LIF and VEGF for 11 days, but after the growth factors were removed, stem cell clones did not produce a significant number of neurons, instead differentiating largely into astrocytes by 14 days. Hence, the soluble factors responsible for the dramatic promotion of stem cell self-renewal and neurogenesis are different endothelial cell-derived factors.

REFERENCES

1. F. Doetsch, *Curr Opin Genet Dev* 13, 543-50 (2003).
2. T. D. Palmer, A. R. Willhoite, F. H. Gage, *J. Comp Neurol* 425, 479-494 (2000).
3. A. Capela, S. Temple, *Neuron* 35, 865-875 (2002).
4. A. Louissaint, Jr., S. Rao, C. Leventhal, S. A. Goldman, *Neuron* 34, 945-960 (2002).
5. G. Breier, U. Albrecht, S. Sterrer, W. Risau, *Development* 114, 521-532 (1992).
6. X. Qian et al., *Neuron* 28, 69-80 (2000).
7. J. O. Suhonen, D. A. Peterson, J. Ray, F. H. Gage, *Nature* 383, 624-7 (1996).
8. D. G. Herrera, J. M. Garcia-Verdugo, A. Alvarez-Buylla, *Ann. Neurol* 46, 867-877 (1999).
9. R. F. Hevner et al., *Neuron* 29, 353-366 (2001).
10. X. Qian, S. K. Goderie, Q. Shen, J. H. Stern, S. Temple, *Development* 125, 3143-3152 (1998).
11. A. Chenn, C. A. Walsh, *Science* 297, 365-9 (2002).
12. A. Chenn, C. A. Walsh, *Cereb Cortex* 13, 599-606 (2003).
13. B. Lu, F. Roegiers, L. Y. Jan, Y. N. Jan, *Nature* 409, 522-525 (2001).
14. S. Hitoshi et al., *Genes Dev.* 16, 846-858 (2002).
15. A. Chojnacki, T. Shimazaki, C. Gregg, G. Weinmaster, S. Weiss, *J. Neurosci.* 23, 1730-1741 (2003).
16. Y. Nakamura et al., *J Neurosci* 20, 283-93 (2000).
17. T. Ohtsuka, M. Sakamoto, F. Guillemot, R. Kageyama, *J Biol Chem* 276, 30467-74 (2001).
18. X. Qian, S. K. Goderie, Q. Shen, J. H. Stern, S. Temple, *Development* 125, 3143-3152 (1998).
19. X. Qian et al., *Neuron* 28, 69-80 (2000).
19. A. Capela, S. Temple, *Neuron* 35, 865-875 (2002).
20. R. Montesano et al., *Cell* 62, 435-445 (1990).

21. J. Jensen et al., *Nat Genet* 24, 36-44 (2000).
22. T. Takahashi, R. S. Nowakowski, V. S. Caviness, Jr., *J Neurosci* 15, 6046-57 (1995).
23. J. Takahashi, T. D. Palmer, F. H. Gage, *J. Neurobiol.* 38, 65-81 (1999).
24. C. A. Wohl, S. Weiss, *J Neurobiol* 37, 281-90 (1998).
25. R. M. Seaberg, D. van der Kooy, *J. Neurosci.* 22, 1784-1793 (2002).
26. T. D. Palmer, J. Takahashi, F. H. Gage, *Mol. Cell Neurosci.* 8, 389-404 (1997).
27. J. Rak, J. Filmus, R. S. Kerbel, *Eur J Cancer* 32A, 2438-50 (1996).
28. G. Seghezzi et al., *J Cell Biol* 141, 1659-73 (1998).
29. B. D. Hoehn, S. I. Harik, A. G. Hudetz, *Brain Res Mol Brain Res* 101, 103-8 (2002).
30. T. Shimazaki, T. Shingo, S. Weiss, *J. Neurosci.* 21, 7642-7653 (2001).
31. K. Jin et al., *Proc. Natl. Acad. Sci. U.S.A* 99, 11946-11950 (2002).
32. Y. Zhu, K. Jin, X. O. Mao, D. A. Greenberg, *Faseb J* 17, 186-93 (2003).
33. V. Tropepe et al., *Neuron* 30, 65-78 (2001).
34. L. H. Strong, *J. Comp. Neurol* 123, 121-138 (1964).

The invention claimed is:

1. A method for obtaining an expanded population of neural stem cells from an original population of neural stem cells, wherein the cells of the expanded population retain the developmental capacity of the original population, the method comprising:
   1) obtaining an original isolated population of neural stem cells; and
   2) culturing said cells in a serum-free medium in the presence of a trophic support selected from the group consisting of:
       a) vascular endothelial cells; and
       b) conditioned media from a vascular endothelial cell culture, in an amount sufficient to stimulate self-renewal of the neural stem cells, to obtain an expanded population of neural stem cells that retain the developmental capacity of the original population.

2. The method of claim 1 wherein the neural stem cells are cultured non-contiguously with vascular endothelial cells.

3. The method of claim 1 wherein the neural stem cells are grown in the presence of conditioned media from a vascular endothelial cell culture.

4. The method of claim 1, wherein the neural stem cells are obtained from embryonic neural tissue.

5. The method of claim 1 wherein the endothelial cells are primary cells.

6. The method of claim 5 wherein the endothelial cells are pulmonary artery endothelial cells.

7. The method of claim 6, wherein the endothelial cells are bovine.

8. The method of claim 1 wherein the endothelial cells are a cell line.

9. A method for enhancing neurogenesis comprising:
   1) obtaining neural stem cells that can differentiate into neurons; and
   2) culturing said cells in a serum-free medium in the presence of a trophic support selected from the group consisting of:
       a) vascular endothelial cells; and
       b) conditioned media from a vascular endothelial cell culture, in an amount sufficient to stimulate self-renewal of the neural stem cells to obtain an expanded population of neural stem cells wherein the neural stem cells retain the ability to differentiate into neurons.

10. The method of claim 9 comprising a further step of removing said trophic support, wherein said expanded population of neural stem cells are allowed to differentiate into neurons.

11. The method of claim 9 wherein the neural stem cells are cultured non-contiguously with vascular endothelial cells.

12. The method of claim 9 wherein the neural stem cells are grown in the presence of conditioned media from a vascular endothelial cell culture.

13. The method of claim 9 wherein said neural stem cells differentiate into projection neurons.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial
<220> FEATURE:
<223> OTHER INFORMATION: primer

<400> SEQUENCE: 1
tcaacacgac accggacaaa cc                                          22

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
ggtacttccc caacacgctc gc                                          22

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
aagtaccgtg gcggtggaga t                                           21

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
gagtaaccct cgctgtagtc c                                           21

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
atgtttgtga tgggtgtgaa                                             20
```

```
<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
tgggagttgc tgttgaagtc                                                   20
```